(12) United States Patent
Farrell et al.

(10) Patent No.: US 7,878,198 B2
(45) Date of Patent: Feb. 1, 2011

(54) METHODS AND APPARATUS FOR MONITORING THE CARDIOVASCULAR CONDITION OF PATIENTS WITH SLEEP DISORDERED BREATHING

(76) Inventors: Michael Farrell, 11736 Spruce Run Dr., San Diego, CA (US) 92131; Malcolm Hebblewhite, 235 Market St., San Diego, CA (US) 92101; Diedre Stewart, 4165 Rochester Rd., San Diego, CA (US) 92113; Ann Tisthammer, 16652 S. 38$^{th}$ Pl., Phoenix, AZ (US) 85048; Maya Vance, 13968 W. 148$^{th}$ St., Olathe, KS (US) 66062; Robin Randolph, 9320 Kulsa Rd., Cascade, CO (US) 80809

( * ) Notice: Subject to any disclaimer, the term of this patent is extended or adjusted under 35 U.S.C. 154(b) by 257 days.

(21) Appl. No.: 10/598,914

(22) PCT Filed: Mar. 30, 2005

(86) PCT No.: PCT/US2005/010663

§ 371 (c)(1),
(2), (4) Date: Sep. 14, 2006

(87) PCT Pub. No.: WO2005/096737

PCT Pub. Date: Oct. 20, 2005

(65) Prior Publication Data

US 2007/0161913 A1    Jul. 12, 2007

Related U.S. Application Data

(60) Provisional application No. 60/557,846, filed on Mar. 31, 2004.

(51) Int. Cl.
*A61M 11/00* (2006.01)
(52) U.S. Cl. .............................. 128/204.18; 128/204.21

(58) Field of Classification Search ............ 128/204.18, 128/200.24, 200.26, 204.21, 204.26
See application file for complete search history.

(56) References Cited

U.S. PATENT DOCUMENTS

| 5,105,354 A | 4/1992 | Nishimura |
| 5,259,373 A | 11/1993 | Gruenke et al. |
| 5,275,159 A | 1/1994 | Griebel |
| 5,769,084 A | 6/1998 | Katz et al. |

(Continued)

FOREIGN PATENT DOCUMENTS

DE        19538473        4/1997

*Primary Examiner*—Steven O Douglas
(74) *Attorney, Agent, or Firm*—Gottlieb, Rackman & Reisman, PC (57) ABSTRACT

A method for relating to each other cardiovascular and sleep disordered breathing conditions of a patient. The patient's heart rate and/or detailed echocardiogram data is monitored and recorded continuously or periodically together with sleep disordered breathing information on similar time scales. Changes in the patient's heart rate associated with changes in sleep disordered breathing can then be observed. More specifically, positive airway pressure at therapeutic levels for treatment of sleep disordered breathing is applied while events associated with the treatment of the patient's sleep disordered breathing are detected and recorded. At the same time, information concerning the cardiovascular condition of the patient is stored and the stored information concerning the cardiovascular condition of the patient and the recorded events associated with the treatment of the patient's sleep disordered breathing are related to each other.

7 Claims, 4 Drawing Sheets

U.S. PATENT DOCUMENTS

| | | | |
|---|---|---|---|
| 5,974,340 A * | 10/1999 | Kadhiresan | 607/18 |
| 6,186,142 B1 * | 2/2001 | Schmidt et al. | 128/204.23 |
| 6,532,959 B1 | 3/2003 | Berthon-Jones | |
| 6,539,940 B2 | 4/2003 | Zdrojkowski et al. | |
| 6,662,032 B1 | 12/2003 | Gavish et al. | |
| 6,893,405 B2 * | 5/2005 | Kumar et al. | 600/538 |
| 2004/0111040 A1 * | 6/2004 | Ni et al. | 600/534 |
| 2005/0065567 A1 * | 3/2005 | Lee et al. | 607/17 |
| 2005/0115561 A1 * | 6/2005 | Stahmann et al. | 128/200.24 |

* cited by examiner

METHODS AND APPARATUS FOR MONITORING THE CARDIOVASCULAR CONDITION OF PATIENTS WITH SLEEP DISORDERED BREATHING

This application claims the benefit of U.S. provisional application No. 60/557,846 filed on Mar. 31, 2004.

FIELD OF THE INVENTION

This invention relates to methods and apparatus for treating and monitoring sleep disordered breathing ("SDB") in patients with cardiovascular disease or otherwise monitoring the cardiovascular condition of SDB patients.

BACKGROUND OF THE INVENTION

"Sleep-disordered breathing" generally refers to types of breathing disruption that occur during sleep. The most common form of sleep disordered breathing is obstructive sleep apnea ("OSA"). OSA affects approximately 20 million Americans—as many as asthma or diabetes. Less than 10% of people with OSA have been diagnosed and fewer have been treated. Loud, intermittent snoring, apneas, and hypopneas characterize OSA. Because the symptoms of sleep apnea present themselves as a result of a precursor, SDB has become the general term used to describe any disease state that manifests apneas and/or hypopneas during sleep. Apneas and hypopneas interfere with gas exchange, fragment sleep, and frequently cause oxygen desaturations. In severe cases, patients may experience these oxygen desaturations and arousals from sleep hundreds of times each night.

The most common treatment of SDB is to administer continuous positive airway pressure (CPAP). The use of nasal CPAP to treat OSA was invented by Sullivan and taught in U.S. Pat. No. 4,944,310. Briefly stated, CPAP treatment acts as a pneumatic splint of the airway by the provision of a positive pressure, usually in the range 4-20 cm $H_2O$. The air is supplied to the airway by a motor driven blower that is coupled via an air delivery hose to a nose (or nose and/or mouth) mask sealed with the patient's face. More sophisticated forms of CPAP treatment may be provided by bi-level ventilators, proportional assist ventilators and servo-controlled ventilators. Such devices are typically used by the patient on a daily basis before and during sleep.

For example, nasal CPAP treatment of OSA may involve the use of an automated blower, such as the AUTOSET T™ device or AUTOSET SPIRIT™ available from ResMed Ltd. Examples of suitable nasal CPAP masks are the MIRAGE™ nasal mask and the MIRAGE™ full face mask also available from ResMed Ltd. The AUTOSET T™ device continuously monitors the state of the patient's airway and determines an appropriate pressure to treat the patient, increasing it or decreasing it as necessary. Alternatively, bi-level pressures are delivered to the patient as in the VPAP II™ devices also available from ResMed Ltd. Some of the principles behind the operation of the AUTOSET T™ and VPAP II™ devices are described in U.S. Pat. No. 5,704,345. The entire disclosure of U.S. Pat. No. 5,704,345 is incorporated herein by reference. Other forms of pressure treatment are available such as that which is delivered in accordance with a smooth pressure waveform template and a continuous phase variable to provide comfortable pressure support substantially in phase with the patient's respiratory cycle. The device is the subject of U.S. Pat. No. 6,532,957, the entire disclosure of which is hereby incorporated by reference.

In May 2000, a study in the New England Journal of Medicine indicated a profound link between SDB and hypertension, independent of other relevant risk factors. Hypertension as a disease has been estimated to afflict more than 25% of the population over 44 years of age. Left untreated, it leads to cardiovascular diseases such as heart attacks, stroke, coronary artery disease and heart failure. Collectively, cardiovascular disease ("CVD") is now recognized as the major cause of death and disability in modern societies. Studies have shown that over 60% of stroke, 50% of heart failure, 35% of hypertensive and 30% of coronary artery disease patients have SDB.

In general, CVDs are diseases that have an impact on the correct functioning of the heart and blood vessels. In addition to cerebrovascular diseases (stroke), other significant CVDs include myocardial infarction (heart attack), congestive heart failure ("CHF"), transient ischaemic attacks ("TIA") and peripheral vascular diseases, to name a few. As a whole it has been estimated that about 17 million people die of CVDs annually. Early diagnosis and treatment of CVDs can be a major factor in reducing mortality associated with CVDs.

CPAP devices have in the past been used for the treatment of SDB in CVD patients. In one such device a form of pressure treatment has been directed at treatment of cardiac failure and Cheyne-Stokes breathing. In a device designated AUTOSET CS™, also provided by ResMed Ltd., pressure support is varied in phase with patient respiration in such a manner to oppose the waxing and waning changes in patient respiration that characterize Cheyne-Stokes breathing. The device is the subject of U.S. Pat. No. 6,532,959, the entire disclosure of which is incorporated herein by reference.

As disclosed by Farrell et al. in U.S. Pat. No. 6,336,454, CPAP treatment has also been recognized as a beneficial treatment of stroke. The use of CPAP treats stroke patients by improving arterial blood oxygen levels and reducing arterial carbon dioxide levels as well as improving auto-regulation of, for example, blood pressure, cardiac output and ventilation. Improvements in morbidity, such as rate and degree of recovery of vital signs and patient stabilization in the acute phase, is an expected benefit.

Also, U.S. Pat. No. 5,794,615 teaches a system including methods and apparatus for treatment of congestive heart failure. The system involves applying separate and independent gains to flow rates of pressurized gas delivered to a patient during inspiratory and expiratory phases of a respiratory cycle. The pressure support is disclosed as reducing cardiac pre-load and after load.

In short, there are many devices that can be used for treating SDB in patients that have cardiovascular disease. Nevertheless, despite a recognized need for early treatment or diagnosis of CVD patients and a lack of complete understanding of the mechanics of these diseases, little has been done to take advantage of the patient information monitoring potential of such CPAP devices that would exploit the substantial presence of these devices in the lives of SDB patients who may also be CVD patients or potential CVD patients. In short, there exists a need to track or monitor information related to such patients that would promote early treatment and diagnosis of CVD as well as further the understanding of SDB.

SUMMARY OF THE INVENTION

It is an objective of the invention to provide methods and apparatus for treating respiratory disorders in cardiovascular disease patients or potential cardiovascular disease patients.

It is a further objective to provide methods and apparatus that assist in the management or monitoring of the cardiovascular condition of such patients to assist with diagnosis or treatment of related diseases.

Other objectives will be apparent to those skilled in the art from a review of the description of the invention as contained herein.

In accordance with one aspect of the invention there is provided apparatus comprising a sleep disordered breathing treatment unit and a unit for monitoring the patient for indications of cardiovascular disease.

The invention provides methods and apparatus useful for cardiovascular disease patients or potential cardiovascular disease patients with sleep disordered breathing. Preferably, the device is capable of delivering positive airway pressure at therapeutic levels for treatment of sleep disordered breathing. The device can be configured with one or more protocols that may be utilized in the provision of such pressure treatment. Over the course of one or more sessions of such treatment, the device may be configured to detect and record events associated with sleep disordered breathing, such as apnea, hypopneas, partial obstruction, snoring, pressure versus time, flow versus time, and leak for future analysis.

Additionally, the device is configured to detect or prompt and accept as input additional information concerning the cardiovascular condition of the patient including, for example, blood pressure, heart rate, oximetry data, electrocardiogram data, Holter Analysis results (including arrhythmia and heart-rate variability summaries), body mass index (including height and weight data), Left Ventricular Ejection Fraction ("LVEF"), six-minute walk data, B-type natriuretic peptide ("BNP"), cardiac output data, $VO_2$ max data, New York Heart Association Class ("NYHA"), ACC/AHA Heart Failure Stage, Quality of Life data (including, for example, Epworth Sleepiness Scale, Berlin Questionnaire, Minnesota Living with Heart Failure Questionnaire, and Kansas City Cardiomyopathy Questionnaire), peripheral arterial tone ("PAT"), and Key neuro-hormonal levels (e.g., catecholamine levels).

Such data may be continuously or periodically recorded or entered into the device relative to time. With such data in the device associations may be observed or made between the cardiovascular information and sleep disordered breathing related events on a common time scale so that changes that occur approximately or substantially in common may be observed or tracked. Such data may be retrieved from or viewed on the device or accessed remotely by a physician or clinician for purposes of monitoring or diagnosis of the patient's SDB and/or a potential CVD.

Another aspect of the invention is a combination of products, services and business pathways for providing care of SDB and CVD co-morbid patients.

Other aspects of the invention are described in the following detailed description.

DESCRIPTION OF THE INVENTION

Figure 1:
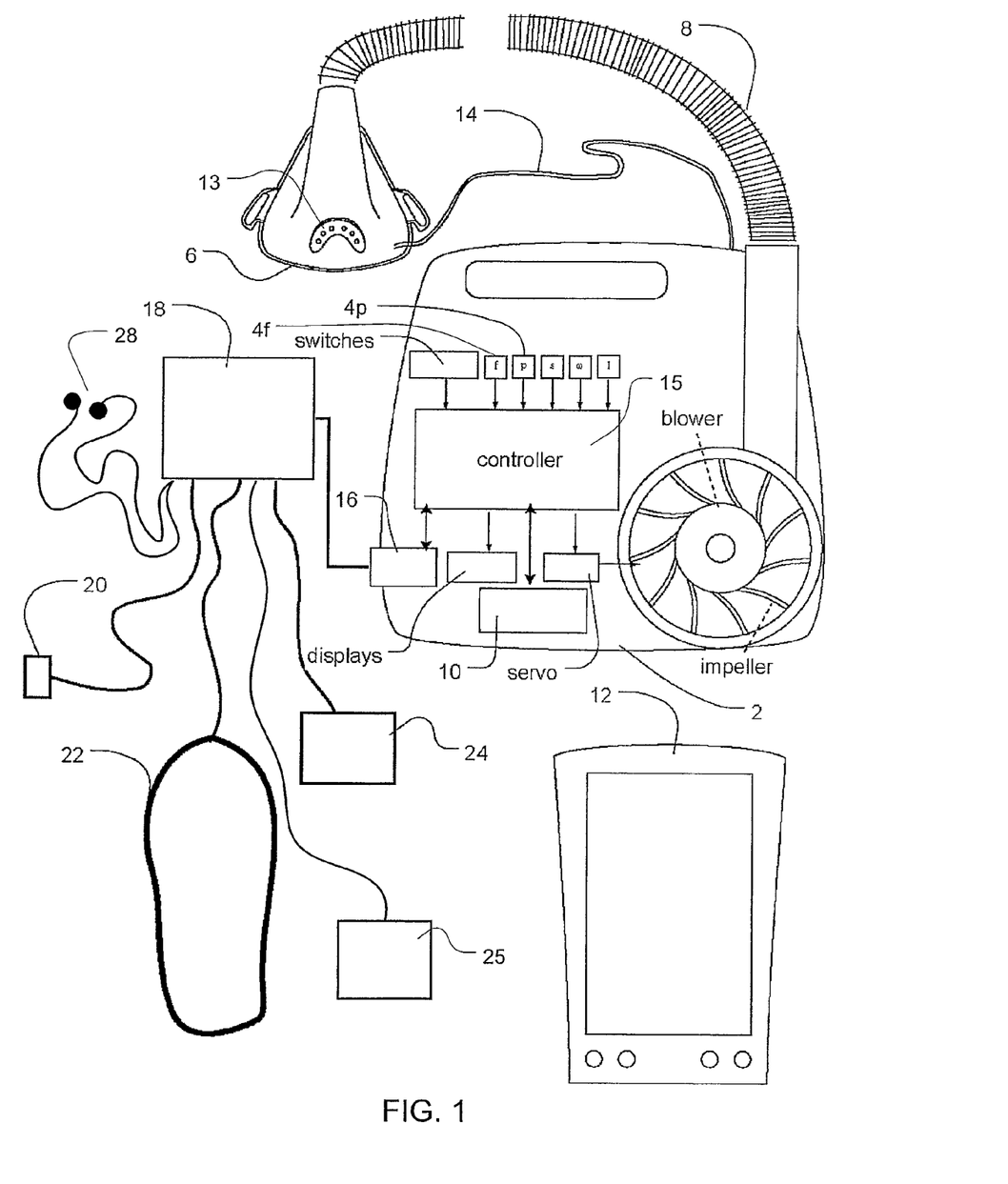
FIG. 1 shows an apparatus according to the invention.

With reference to FIG. 1, the invention involves a pressure delivery device that may include a servo-controlled blower 2, a mask 6, and an air delivery conduit 8 for connection between the blower 2 and the mask 6. Exhaust gas is vented via exhaust 13. Optionally, a flow sensor 4f and/or pressure sensor 4p may also be utilized in which case mask flow may be measured using a pneumotachograph and differential pressure transducer or similar device to derive a flow signal F(t), and mask pressure is measured at a pressure tap using a pressure transducer to derive a pressure signal $P_{mask}(t)$. The pressure sensor 4f and flow sensor 4p have only been shown symbolically in FIG. 1 since it is understood that those skilled in the art would understand how to measure flow and pressure. Flow F(t) and pressure $P_{mask}(t)$ signals are sent to a controller or microprocessor 15 to derive a pressure request signal $P_{request}(t)$. Alternatively, a flow signal f(t) and pressure signal $P_{mask}(t)$ may be estimated or calculated in relation to the blower motor by monitoring current supplied to the motor and/or the speed of the motor as disclosed in U.S. Pat. Nos. 5,740,795, 6,332,463 or 6,237,593 without the provision of flow and pressure sensors as described above. Optionally, the blower motor speed may be held generally constant and pressure changes in the mask may be implemented by controlling an opening of a servo-valve that may variably divert/vent or deliver airflow to the mask.

A controller 15 or processor is configured and adapted to implement the methodology described in more detail herein and may include integrated chips, a memory and/or other instruction or data storage medium. For example, programmed instructions with the control methodology may be coded on integrated chips in the memory of the device or such instructions may be loaded as software. With such a controller, the apparatus can be used for many different pressure treatment therapies simply by adjusting the pressure delivery equation that is used to set the speed of the blower or to manipulate the venting with the release valve.

The apparatus preferably also includes a communication port or module 10, for example, a wireless communication transceiver and/or a network card, for communication with other devices or computers such as hand-held display and control devices 12. The apparatus may further include additional interface 16 for connection to additional diagnosis or patient information gathering devices. For example, a diagnosis unit may optionally include a pulse oximeter 20, respiratory movement sensors 22 such as a chest band, EEG & ECG 24, EOG 25 and/or electrodes 28 for detecting cardiac rhythm. The oximeter may optionally be included in the main blower housing. There is a sense tube 14 connected to the main housing of the blower to the mask that allows the apparatus to sense oxygen concentration and pressure levels in the mask 6. Optionally, an automated $PCO_2$ measurement device 21 or other non-invasive blood gas monitor/device for measuring $PCO_2$ may be linked to provide an input data signal to the microprocessor 16, for example, a device as taught in U.S. Pat. No. 5,630,413, the disclosure of which is incorporated by reference. Other automated measuring devices may also be included with the diagnosis unit as it relates to measuring other cardiovascular related information from the patient. In this regard, the device may, for example, be configured to communicate/receive such information from its own display (e.g., LCD screen) and input device (e.g., keypad or buttons) or via telemetry or other communication link from a blood pressure monitor, heart rate monitor, oximetry monitor, ECG device, ECG Event Monitor, Holter monitor, automated tape measure, automated weight scale, treadmill device, blood analyzer device, cardiac output analyzer device, $VO_2$ max data device or peripheral arterial tone assessment device. Those skilled in the art will recognize the types of information that may be generated by such devices.

Other optional input and/or output devices 22 may be included to display output signals and enter input signals for the microprocessor 16. Various appropriate input and output devices such as keypads and display screens and other alternatives are known in the art.

While this apparatus is generally described as a single unit, it is understood that a combination of devices and/or computers linked by any available communications method may be used to accomplish the goals of the invention. For example, the apparatus can interface with a variety of hand-held devices such as a Palm Pilot via wireless communication or it may interface with a network for transmission between the devices. With such a device or system, a physician may, for example, remotely monitor, analyze or record the status or data history of a patient. For example, remote devices may send to or retrieve from the apparatus any desired cardiovascular or other information. Such information may even be transmitted from the apparatus to a database of one or more patients. Furthermore, the treatment program that is being run on the patient can be monitored and changed remotely. In the event patient data is transmitted over open networks, the data may be encrypted for purposes of patient confidentiality.

Pressure Treatment Protocols

Figure 2:
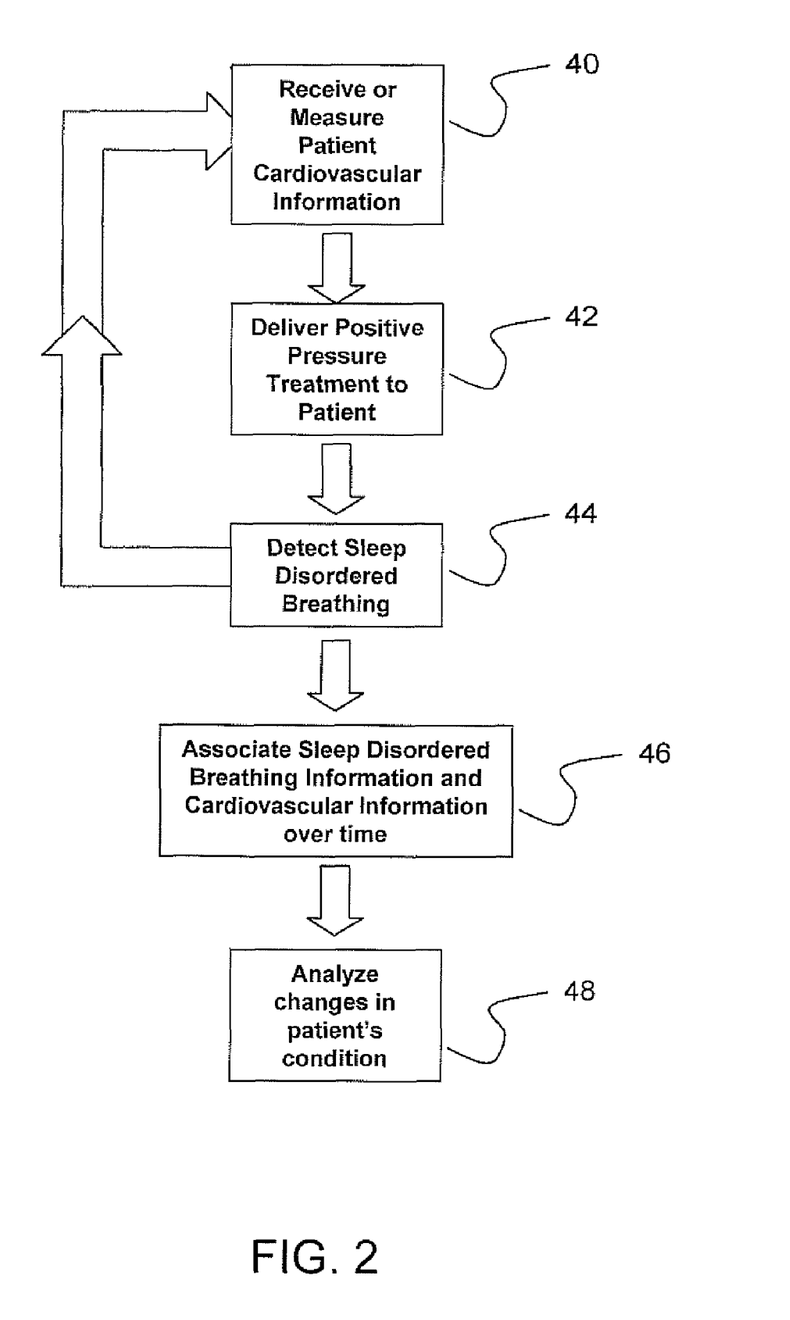
FIG. 2 is a flow chart of a method for monitoring patient cardiovascular information.

As illustrated by step 42 in the flow chart of FIG. 2, the apparatus incorporates various pressure treatment protocols that may be used to treat the condition of the patient. For example, in one mode, the device provides a generally constant pressure throughout a breathing cycle that may be therapeutic pressure or changes to such pressure set to treat SDB. In another mode, the apparatus provides a higher pressure to the mask during the inspiratory portion of the breathing cycle, a so-called IPAP (inspiratory positive airway pressure), and a lower pressure to the mask during the expiratory portion of the breathing cycle, a so-called EPAP (expiratory positive airway pressure). Alternatively, the treatment delivered by the apparatus can smoothly vary in accordance with patient respiration to provide a smooth pressure waveform. For example, the device calculates a continuous phase variable to provide support in phase with the patient's breathing cycle and calculates the pressure to be delivered in accordance with a pressure waveform template. The delivery of such pressure is disclosed in U.S. Pat. No. 6,532,957. Still alternatively, pressure may be supplied in proportion to patient respiratory airflow.

In yet another form, pressure support is varied in phase with patient respiration in such a manner to oppose the waxing and waning changes in patient respiration that characterize Cheyne-Stokes breathing. The methodology for such treatment is disclosed in U.S. Pat. No. 6,532,959.

Optionally, the therapeutic pressure levels of the above protocols may be preset by a clinician or may be automatically adjusted or set by automatic detection of SDB related events, such as apneas (obstructive or central), hypopneas, partial obstruction, snoring, etc. as disclosed in U.S. Pat. 5,704,345 (Berthon-Jones). For example, the IPAP or EPAP levels may be adjusted by the automated determination to hunt for a minimal pressure that will be required to prevent or alleviate obstruction. Other alternative methods to vary the therapeutic level of the pressure for treatment to a patient and to detect SDB events may be utilized and are known in the art.

In providing these treatment methodologies, an accurate determination of respiratory airflow is important. Thus, the determined flow rate of air to the patient may be adjusted to account for the effect of leak. To this end, leak airflow may be determined by using a method such as taught in U.S. Pat. No. 6,152,129 (Berthon-Jones), the entire disclosure of which is incorporated herein by reference. Leak data may also be recorded over time and stored in the device. Other known methods for determining leak may also be used by the device.

Other forms of pressure treatment will be known to those skilled in the art and may be implemented by the device.

Monitoring of Sleep Disordered Breathing Related Information

Preferably, the device provides efficacy tracking by detecting and recording or scoring SDB events or related information or indices over time, for example, by tracking or detecting central apneas, obstructive apneas, hypopneas, partial obstructions (e.g., flow flattening) or snoring. This is illustrated in step 44 of FIG. 2. Similarly, pressure and/or flow versus time data may also be recorded for analysis. In so doing, the device preferably performs compliance tracking in which the time on and time off of the mask are recorded with SDB related events for evaluation by statistical summaries and charting. Methods for detecting and recording such information are known in the art, and may be implemented as described in U.S. Pat. No. 5,704,345.

For example, the device may record AHI (apnea hypopnea index) over time or during particular time periods such as session-by-session, day-by-day, hour-by-hour, etc. In one embodiment of the invention an AHI scoring scheme may be implemented as follows:

(i) An apnea is scored if a 2 second moving average ventilation drops below 25% of a recent average ventilation (time constant=100s) for at least 10 consecutive seconds, (ii) An hypopnea is scored if the 8 second moving average drops below 50% but not more than 25% of the recent average ventilation for 10 consecutive seconds.

Similarly, the device may determine an index comparing central apneas versus obstructive apneas as disclosed in U.S. Pat. No. 6,832,609, the entire disclosure of which is incorporated by reference herein.

These events may be recorded with the time they occur or added to a total for a particular time period. Those skilled in the art will recognize other methods or modifications for detecting sleep disordered breathing information such as hypopneas or apneas and determining an AHI over time or within time periods.

Monitoring of Cardiovascular Condition

As previously noted and illustrated in step 40 of FIG. 2, the device is configured to receive information relating to cardiovascular information for the patient. Thus, a device of the invention preferably includes input devices for receiving or recording such based on the condition of the patient, continuously or periodically, so that preferably, as illustrated in step 46 of FIG. 2, such information may be associated with changes in the sleep disordered breathing related information over time. Embodiments of the invention may include automated measuring apparatus that can generate signals associated with the automatically determined cardiovascular information for a processor of the device. Alternatively, the device may be pre-programmed to prompt or query for such information on a display or from another remote device, before use and/or periodically such as monthly, after three or six months, or some other timed period which may be based on use of the device (e.g., after 30 nights of use, etc.), so that such information may be measured or determined separately and input by a user on a keypad or other data entry device. In relation to cardiovascular related questionnaires, queries may be pre-programmed into the device and appropriate responses can be input by the patient in response to prompting by the device.

In one embodiment, an apparatus of the invention may include automated blood pressure monitoring apparatus that may continuously or periodically monitor or measure blood pressure and record such information such as in an overnight summary versus time. Alternatively, the device may prompt for input of such information on a display and keypad without the provision of such an automated device. Such information may then be charted alone or in association with sleep disordered breathing related information or events, such as an AHI, on a comparable or similar time scale so that related changes may be observed or noted.

In one embodiment, the device may monitor and record heart rate and/or detailed echocardiogram data continuously or periodically. Such information may be detected by filtering cardiogenic flow from a respiratory flow signal as disclosed in U.S. Pat. No. 5,704,345 or by another available heart rate detector. By recording such information over time, alone or on a similar time scale as sleep disordered breathing information, changes in heart rate may be observed or associated with changes in sleep disordered breathing to assist in tracking the condition of the patient.

Similarly, various embodiments of the device may optionally measure, prompt for and/or record/monitor additional cardiovascular information including oximetry data, blood sugar data, blood pressure data, electrocardiogram data, Holter Analysis results (including, e.g., arrhythmia, heart-rate and/or variability summaries), Body Mass Index, height and weight data, Left Ventricular Ejection Fraction (LVEF), Six-minute walk data, B-type natriuretic peptide (BNP), Cardiac Output data, $VO_2$ max data, New York Heart Association Class (NYHA), ACC/AHA Heart Failure Stage, Quality of Life data (including, e.g., Epworth Sleepiness Scale, Berlin Questionnaire, Minnesota Living with Heart Failure Questionnaire, and/or Kansas City Cardiomyopathy Questionnaire), Peripheral arterial tone (PAT) and Key neuro-hormonal levels (e.g., catecholamine levels).

Depending on the patient using the device, some or all of the above-listed cardiovascular information may be monitored by the device. In this regard, the device may be configured to monitor all of this information but the physician can preset the device to select one or more of the features for particular patients, which will then be monitored during their use. In one embodiment, the device is pre-programmed with associated sets or groups of data selected from the cardiovascular information that are pertinent for specific cardiovascular patients. By selecting a particular patient type, the device can automatically be configured to monitor the pertinent cardiovascular information from the associated set or group of monitored data without monitoring unnecessary cardiovascular information for the particular patient. For example, a hypertension patient may be monitored for blood pressure, heart rate and Body Mass Index or a heart failure patient may be monitored for LVEF, heart rate and cardiac output data, a diabetic may be monitored for blood sugar, etc. Those skilled in the art will understand which cardiovascular information is preferably associated with the different types of cardiovascular patients.

With the collection of such cardiovascular information being managed by the pressure treatment device, for example, on a night-by-night or week-by-week basis as it relates to the particular information being collected, a physician or clinician may periodically access a substantial source of information for study or analysis, as illustrated by step 48 of FIG. 2. Preferably, the cardiovascular and SDB information may be periodically remotely transferred to the physician or it may be accessed directly through displays on the device. In this way, a physician may keep up with and observe the changing cardiovascular condition of the patient with minimal direct oversight or intervention. Optionally, the device can be programmed with thresholds for comparison to the recorded cardiovascular information to trigger an alarm or send a message or generate a warning for the user, clinician or physician either directly on the device, or remotely, for example, over a secure electronic network to a database. For example, if the recorded or detected heart rate falls below an acceptable level, a warning or alarm may be generated. Similarly, if changes in weight, arrhythmia, blood pressure, blood sugar, heart variability, ECG data, etc. are recorded, automated warnings, alarms or messages may be generated by the device and manual or automated changes to the control of the device may be made such as a change in treatment protocol or a change to the set of monitored cardiovascular information such that additional cardiovascular information may be monitored. For example, the device may switch from monitoring hypertension associated cardiovascular information to monitoring congestive heart failure associated cardiovascular information if changes in the hypertension related monitoring data suggest that the patient's cardiovascular condition is deteriorating. Similarly, the device's treatment protocol may switch from a standard bi-level protocol to one that delivers servo-controlled pressure changes intended to reduce waxing and waning changes associated with Cheyne-Stokes breathing.

Monitoring patients is an important aspect of management of cardiovascular disease. In accordance with an embodiment of the invention, one can take advantage of the long-term use of nasal CPAP devices (almost every night for the rest of the patient's life) to monitor patients for many years. Thus it is hoped that early detection can lead to improved outcomes of a patient.

While the invention has been described with various alternative embodiments and features, it is to be understood that the embodiments and features are merely illustrative of the principles of the invention. Those skilled in the art would understand that other variations can be made without departing with the spirit and scope of the invention. For example, cardiovascular related treatment or diagnostic devices may be implemented to query for or measure SDB related information for the purpose of detecting SDB or otherwise determining a relationship between the cardiovascular condition of the patient and SDB. For example, a Holter Monitor or cardiac event monitor may be configured or programmed to prompt a patient with an SDB questionnaire. Thus, in one embodiment, the device may prompt a user with such questions as:

1. Do you snore?
2. Are you excessively tired during the day?
3. Do you wake during the night feeling breathless?
4. Have you been told you stop breathing during sleep?
5. Do you have a history of hypertension?

In response to the answers from the user input into the device, for example, if yes to two or more of these questions is received, the device may record, transmit or generate a warning to the user or physician to consider referral to a clinician or other physician for the purpose of undertaking a sleep diagnostic study to access the potential for SDB. In a more complex embodiment, a more detailed assessment of SDB related information may be implemented by the device. For example, it may prompt for the following:

Gender: (Male or Female)
Age Group: 18-39 40-59 60-79 80+
Height: (feet, inches)
Weight: (pounds)

1. Do you snore regularly?
2. Are you excessively sleepy during the day?
3. Do you wake during the night feeling breathless?
4. Have you been told you stop breathing during sleep?
5. Do wake up feeling un-refreshed after a night's sleep?

6. Do you have a history of hypertension?

7. Is the patients BMI>30?

The number of positive responses may be tallied by the device to generate a SDB index which may be reported to a physician with a warning or other message. Alternatively, the SDB index may be compared to one or more thresholds and the degree of the need for a follow-up SDB study may be contained in a message or warning to the physician or user. For example, if the tally is 1 or 0, the message may identify that there is a low likelihood that the patient has an SDB condition or would need to follow-up with a sleep study. A higher tally, such as a 4 or higher, may result in a more significant or urgent warning message suggesting that there is a high or higher likelihood of SDB or a need for a full SDB assessment. Such data may be combined with other sleep disordered breathing data recorded by the device, for example, an AHI, if the device is configured to record such data and may be included in the message or warning to the physician or user.

Similarly, other cardiovascular related treatment or diagnostic device may be configured or programmed to make an assessment for SDB related information of the patient, for example, a blood pressure monitor, heart rate monitor, oximetry monitor, Holter Monitor or other ECG device or cardiac event monitor, automated tape measure, automated scale device for weight, treadmill device, blood analyzer device, cardiac output analyzer device, $VO_2$ max data device, peripheral arterial tone device etc.

It should be appreciated that clinicians interested in SDB and those interested in cardiovascular and even other diseases do not usually cross lines and engage in each others' disciplines. The data collected during treatment of SDB can go back many years. This data can be mined and can be used by clinicians interested in other diseases, even without relating such data to events associated with the patient's SDB, yet presently the data is generally not even made available. It is our intention that the data collected over the long term (measured by at least several months) during treatment of SDB will be made available to clinicians treating one or more other diseases that the patients may have. By charging for such data, it is expected that some of the costs associated with treatment of SDB may even be recoverable. (By "clinicians" we include hospitals, insurance companies and others interested in studying data pertaining to patient diseases.)

Business Pathways

Figure 3:
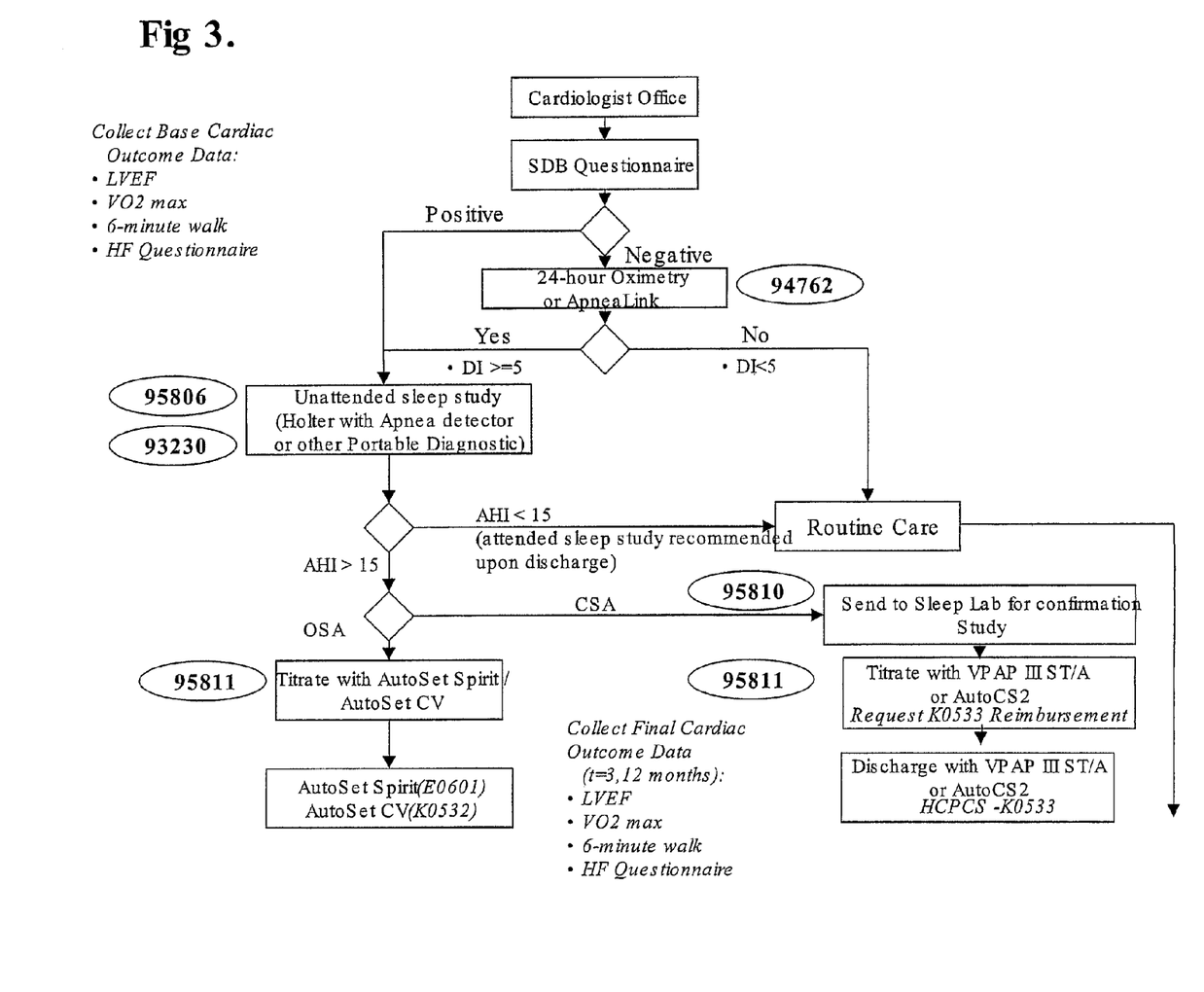
FIG. 3 & 4 are flow charts showing business pathways in accordance with aspects of the invention.
Figure 4:
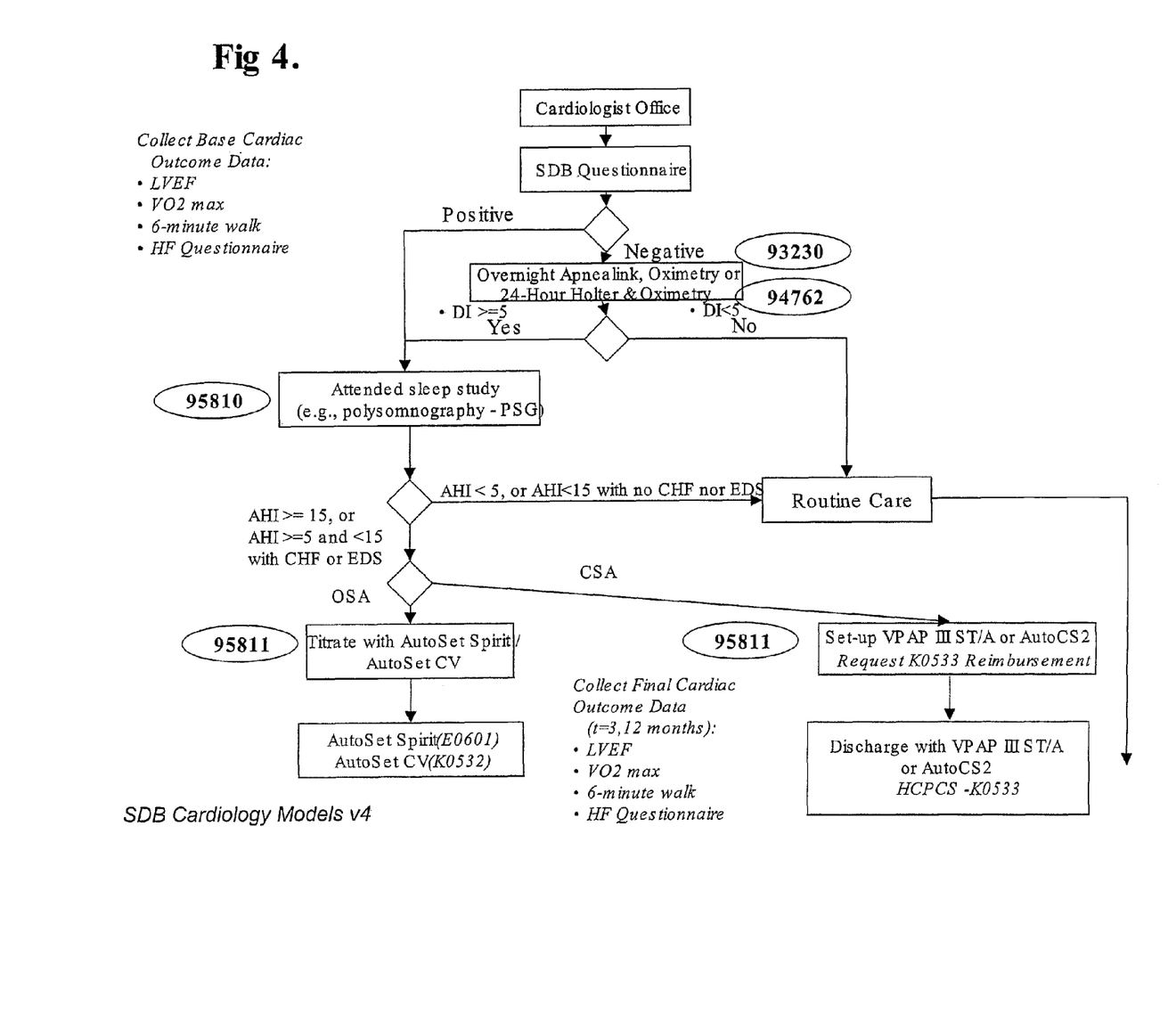

FIGS. 3 & 4 show business pathways in accordance with the invention. Such pathways can be adopted by organizations caring for SBD and CVD co-morbid patients using the equipment shown in FIG. 1. The pathways identify steps to be taken, and identifies the appropriate re-imbursement codes. The pathways can be programmed into portable computers, such as PALM PILOT handheld computers, providing the practitioner with a ready reference for the appropriate codes, as well as allowing a highly skilled medical practitioner (such as a cardiologist) to delegate responsibility to their staff.

For example, in accordance with FIG. 3, in a first step a cardiology patient is given a questionnaire programmed into a handheld computer as discussed above. A positive result from the questionnaire prompts the device to suggest an unattended sleep study, for example with a Holter monitor, as well as reimbursement codes 95806 and 93230. After the sleep study, the results are entered into the computer. A high AHI from the sleep study indicates the potential presence of Obstructive Sleep Apnea (OSA) or Central Sleep Apnea (CSA). Patients with OSA may be treated with an Automatic Positive Airway Pressure (APAP) device such as ResMed's AUTOSET SPIRIT. Alternatively, patients with CSA may be treated with ResMed's VPAP III ST/A device, or Adaptive Servo Ventilation, such as provided by ResMed's AutoSet CS2 device.

In one branch of the flowchart, the decision process includes oximetry or OSA screening by a device such as ResMed's APNEA LINK.

While the invention has been described in several forms, it is to be understood that these forms are merely illustrative of the invention. Those skilled in the art will understand that other variations can be made without departing with the spirit and scope of the invention.

The invention claimed is:

1. A method for determining the cardiovascular condition of a patient relative to a patient's sleep disordered breathing while treating sleep disordered breathing comprising the steps of:

delivering positive airway pressure at therapeutic levels for treatment of sleep disordered breathing with a pressure delivery device, detecting and recording breathing-related events associated with the treatment of the patient's sleep disordered breathing, adjusting delivery of positive airway pressure based on detected events, storing information concerning the breathing and cardiovascular condition of the patient and delivered positive airway pressure over time, correlating the cardiovascular condition of the patient, the patient's breathing, and treatment of the patient's sleep disordered breathing, and determining changes to said patient's cardiovascular condition relative to changes in breathing and changes in delivery of positive airway treatment.

2. A method for monitoring the cardiovascular condition of a patient while treating sleep disordered breathing in accordance with claim 1 wherein said step of detecting and recording breathing-related events associated with the treatment of the patient's sleep disordered breathing includes detecting and recording data related to at least one of apneas, hypopneas, partial obstructions, snoring, pressure versus time, flow versus time, and leaks.

3. A method for treating respiratory disorders and simultaneously monitoring a patient for indications of cardiovascular disease comprising the steps of:

delivering positive airway pressure at therapeutic levels for treatment of respiratory disorders with a pressure delivery device, detecting and recording as a function of time breathing-related events, storing as a function of time information concerning the cardiovascular condition of the patient, and correlating the cardiovascular condition of the patient, the patient's breathing, and treatment of the patient's respiratory disorders, and determining changes to said patient's cardiovascular condition relative to changes in breathing and changes in delivery of positive airway treatment.

4. A method for treating respiratory disorders and simultaneously monitoring a patient for indications of cardiovascular disease in accordance with claim 3 wherein said step of detecting and recording breathing-related events associated with the treatment of the patient's respiratory disorders includes detecting and recording data related to at least one of apneas, hypopneas, partial obstructions, snoring, pressure versus time, flow versus time, and leaks.

5. A method for relating to each other cardiovascular and sleep disordered breathing conditions of a patient with a pressure delivery device which records patient condition comprising the steps of
monitoring and recording heart rate and/or detailed echocardiogram data continuously or periodically
together with patient breathing and sleep disordered breathing treatment on similar time scales, and
correlate changes in the patient's heart rate with changes in sleep disordered breathing and treatment.

6. The method of claim 1 wherein information concerning the cardiovascular condition of the patient includes information related to one or more of blood pressure, heart rate, oximetry data, electrocardiogram data, Holter analysis results, body mass index, left ventricular ejection fraction (LVEF), cardiac output data, and $VO_2$ max data.

7. The method of claim 3 wherein information concerning the cardiovascular condition of the patient includes information related to one or more of blood pressure, heart rate, oximetry data, electrocardiogram data, Holter analysis results, body mass index, left ventricular ejection fraction (LVEF), cardiac output data, and $VO_2$ max data.

* * * * *